United States Patent
Kreutzmann et al.

(10) Patent No.: US 8,739,777 B2
(45) Date of Patent: Jun. 3, 2014

(54) INHALATION THERAPY DEVICE WITH A NOZZLE NEBULISER

(75) Inventors: Vera Kreutzmann, Seefeld (DE); Frank Kummer, Oberschleißheim (DE); Markus Mornhinweg, Diessen (DE); Sven Rosenbeiger, Starnberg (DE); Titus Selzer, Munich (DE)

(73) Assignee: Pari GmbH Spezialisten für effektive Inhalation, Starnberg (DE)

( * ) Notice: Subject to any disclaimer, the term of this patent is extended or adjusted under 35 U.S.C. 154(b) by 953 days.

(21) Appl. No.: 10/575,933

(22) PCT Filed: Sep. 10, 2004

(86) PCT No.: PCT/EP2004/010140
§ 371 (c)(1),
(2), (4) Date: Nov. 15, 2006

(87) PCT Pub. No.: WO2005/042075
PCT Pub. Date: May 12, 2005

(65) Prior Publication Data
US 2007/0068513 A1   Mar. 29, 2007

(30) Foreign Application Priority Data
Oct. 16, 2003   (DE) .................................. 103 48 237

(51) Int. Cl.
*A61M 11/00*   (2006.01)

(52) U.S. Cl.
USPC .................................. 128/200.21; 128/200.14

(58) Field of Classification Search
USPC ............. 128/200.18, 200.14, 200.21, 200.23, 128/200.16, 203.12, 204.18; 239/337, 338, 239/346

See application file for complete search history.

(56) References Cited

U.S. PATENT DOCUMENTS

| | | | |
|---|---|---|---|
| 3,097,645 A | | 7/1963 | Lester |
| 3,382,871 A | * | 5/1968 | Parry ........................ 128/200.18 |
| 4,300,545 A | * | 11/1981 | Goodnow et al. ........ 128/200.14 |
| 5,301,663 A | | 4/1994 | Small, Jr. |
| 5,490,497 A | * | 2/1996 | Chippendale et al. ... 128/200.14 |
| 5,511,539 A | | 4/1996 | Lien |
| 5,584,285 A | * | 12/1996 | Salter et al. .............. 128/200.21 |
| RE36,070 E | * | 2/1999 | Ballini et al. ............ 128/200.14 |

(Continued)

FOREIGN PATENT DOCUMENTS

| | | |
|---|---|---|
| DE | 1 147 354 | 4/1963 |
| DE | G 89 05 364.8 | 10/1989 |

(Continued)

*Primary Examiner* — Justine Yu
*Assistant Examiner* — Colin W Stuart
(74) *Attorney, Agent, or Firm* — Merchant & Gould P.C.

(57) ABSTRACT

The invention relates to an inhalation therapy device with a nozzle nebuliser, in particular with a nozzle nebuliser having a nozzle element which is easy to clean and is thereby simple and reliable to handle so that the nozzle is not damaged and the geometry of the nozzle is not affected during cleaning. The aerosol generator comprises a nozzle element, said nozzle consisting of at least a first part and a second part, said first part of the nozzle element being made of a more resilient material than said second part of the nozzle element, and said first part of the nozzle element being attached to said second part of the nozzle element. Owing to the resilient material, the nozzle can deform during cleaning and can return to the original shape without altering its initial geometry.

16 Claims, 3 Drawing Sheets

(56) References Cited

U.S. PATENT DOCUMENTS

| | | | |
|---|---|---|---|
| 6,045,058 A * | 4/2000 | Dobbeling et al. | 239/11 |
| 6,129,080 A * | 10/2000 | Pitcher et al. | 128/200.21 |
| 6,338,443 B1 * | 1/2002 | Piper | 239/340 |
| 6,742,724 B2 * | 6/2004 | Duqueroie | 239/328 |
| 6,796,513 B2 * | 9/2004 | Fraccaroli | 239/338 |
| 7,407,118 B2 * | 8/2008 | Sevy | 239/347 |
| 2002/0157663 A1 * | 10/2002 | Blacker et al. | 128/200.21 |
| 2004/0089292 A1 * | 5/2004 | Pollet et al. | 128/200.23 |
| 2004/0227011 A1 * | 11/2004 | Tseng | 239/302 |

FOREIGN PATENT DOCUMENTS

| | | |
|---|---|---|
| DE | 103 48 237 A1 | 5/2005 |
| EP | 0 786 263 A2 | 7/1997 |
| EP | 0 855 224 A2 | 7/1998 |
| WO | WO 2005/042075 A1 | 5/2005 |

\* cited by examiner

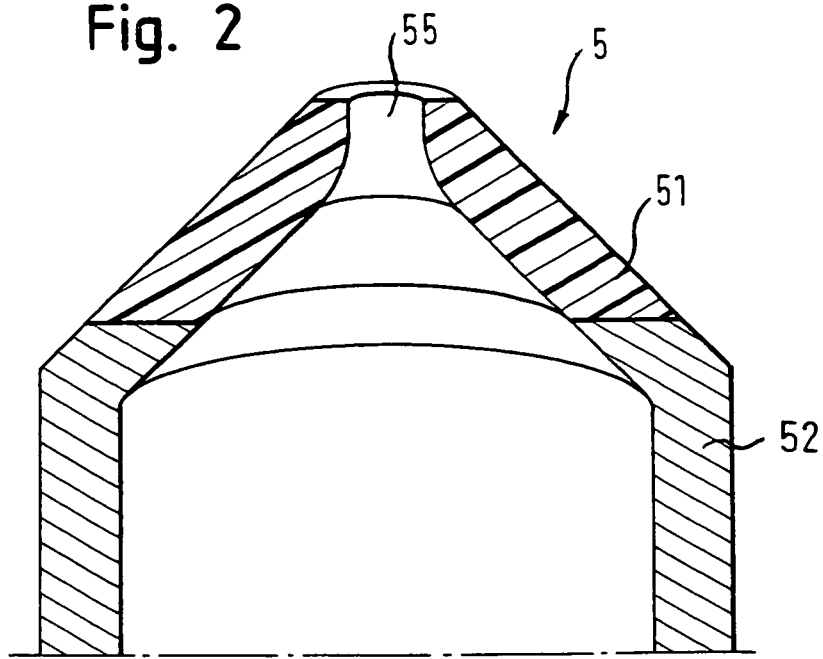
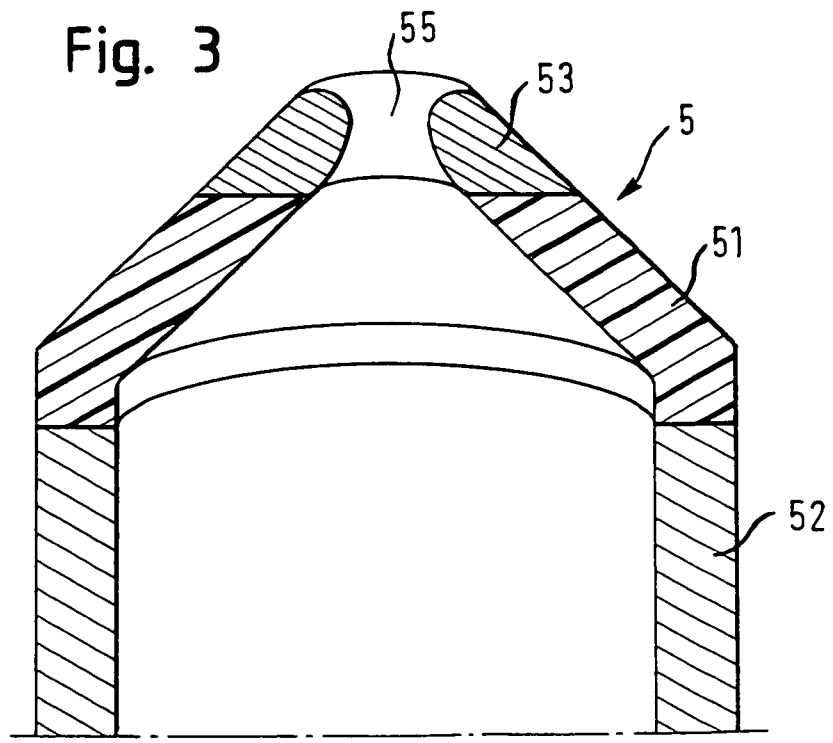

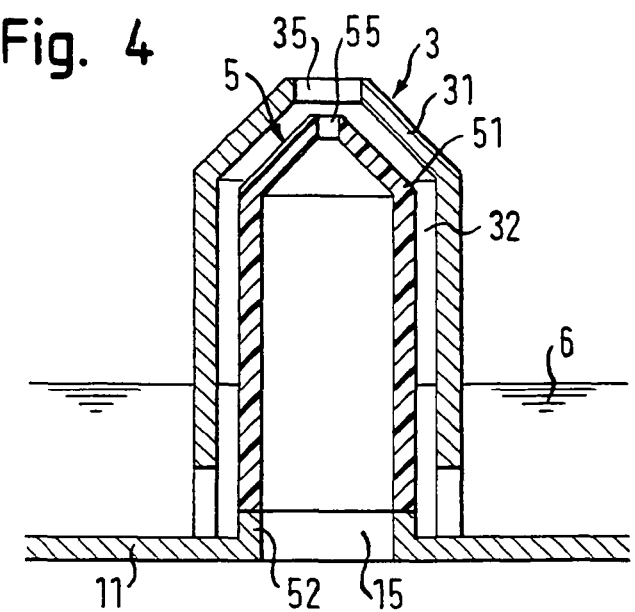
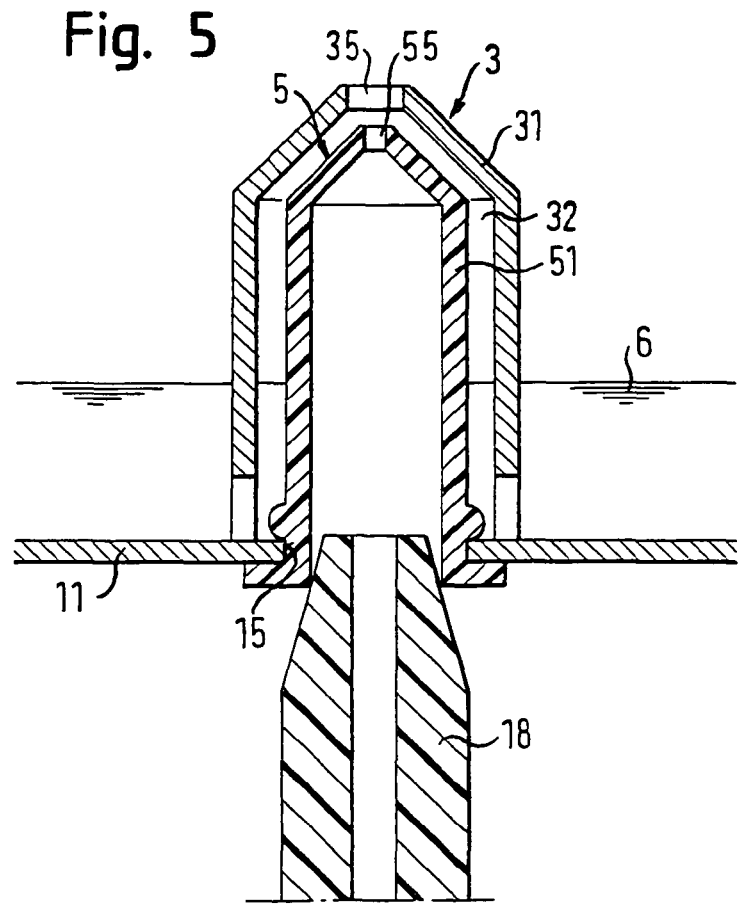

INHALATION THERAPY DEVICE WITH A NOZZLE NEBULISER

BACKGROUND OF THE INVENTION

The invention relates to an inhalation therapy device with a nozzle nebuliser, in particular with a nozzle nebuliser having a nozzle element which is easy to clean and is thereby simple and reliable to handle.

Inhalation therapy devices are used to administer suitable medicaments in the form of an aerosol to patients suffering from disorders of the respiratory tract. By adjusting the droplet size owing to a corresponding design of a nebuliser, it is possible to control those sites (pharynx, bronchi, lungs) at which the medicament is supposed to be deposited. The patient inhales the nebulised medicament through his mouth via a mouthpiece in order to adapt the inhalation therapy device to the patient to an optimum extent.

In order to generate the aerosol with a desired droplet spectrum, it is necessary to precisely realise the geometry of the nebuliser or aerosol generator in order to avoid deviations and modifications over the lifespan of the inhalation therapy device. The geometry of the nozzle element has an essential role in this regard, the nozzle element being part of the aerosol generator. By manufacturing the nozzle element in a precise manner, it is thus ensured that the aerosol has a reproducible droplet spectrum.

In an inhalation therapy device, the aerosol generator and the nozzle are normally exposed to contamination caused by residual medicament, sputum (saliva) and exhalation condensate. To comply with hygiene requirements, especially if the inhalation therapy device is being used by several patients, the components of the nebuliser must therefore be cleaned regularly in order to free them of residual medicament, exhalation condensate and sputum residue. For this purpose, the components of the nebuliser should be designed so that they can be cleaned thoroughly in a simple manner. An inhalation therapy device is normally configured such that it can be cleaned and sterilised in order to remove residual medicament, sputum residue or other such contaminations. For this purpose, the inhalation therapy device can normally be opened or dismantled in such a manner that cleaning and/or sterilisation is possible without any problems.

The nozzle of a nebuliser or an aerosol generator often comprises sharp, precisely manufactured edges, which are necessary to achieve a reproducible droplet spectrum and a good yield, i.e. efficiency of the nebuliser. These geometries of the edges are very sensitive, particularly during cleaning of the nozzle, and they can thus only be cleaned with great care and effort. Finally, it is virtually impossible to prevent damage to the geometry of the nozzle in the medium to long term.

Cleaning of the nebuliser components or the nozzle must, however, be made possible for the reasons already cited above. It must be possible for a patient who is generally unaware of the problem of the sensitive geometry of the nozzle to nevertheless carry out this cleaning without any problems, in particular patients suffering from physical impairments as a consequence of their respiratory disease.

Inhalation therapy devices having nebulisers or aerosol generators are known from the prior art, for example from EP 0 786 263, which can be dismantled such that they can be cleaned, for instance, under running water or sterilised in an autoclave. For this purpose, the inhalation therapy device can be opened such that the nozzle of the aerosol generator is freely accessible and can thus be reached by a cleaning fluid. However, in the case of tightly adhering particles, rinsing with a cleaning fluid is generally not sufficient and therefore mechanical cleaning of the nozzle possibly has to be carried out. This inevitably leads to the use of a cleaning tool, for example a brush or cloth. This considerably increases the risk of damaging the sensitive geometry of the edges of the nozzle and of consequently modifying the desired droplet spectrum of the aerosol generator of the inhalation therapy device. The inhalation therapy device having a nebuliser or an aerosol generator would become ineffective in many cases since the droplet spectrum is essential for the type of therapy.

SUMMARY OF THE INVENTION

The object of the present invention is to eliminate the disadvantages of the inhalation therapy devices of the prior art and to provide an inhalation therapy device having an aerosol generator with a nozzle that is easy to clean owing to its construction and is thereby simple and reliable to handle so that the nozzle is not damaged and the geometry of the nozzle is not affected during cleaning.

This object is solved by means of an inhalation therapy device having a nebulising chamber and an aerosol generator which is arranged such that it releases an aerosol into the nebulising chamber, said aerosol generator comprising a nozzle element, with the nozzle consisting of at least a first part and a second part, said first part of the nozzle element being made of a more resilient material than the second part of the nozzle element, and the first part of the nozzle element being attached to the second part of the nozzle element.

The first part of the nozzle element advantageously has a cross-section which tapers further than that of the second part of the nozzle element.

The first part of the nozzle is advantageously made of silicone rubber or a thermoplastic elastomer (TPE). The first part of the nozzle element is advantageously produced together with the second part of the nozzle element in a two-component method, the first part of the nozzle element thereby being moulded on the second part of the nozzle element.

The first part of the nozzle element advantageously contains the nozzle outlet.

According to a further embodiment, the nozzle advantageously comprises a third part, which contains the nozzle outlet.

The third part of the nozzle element advantageously has a cross-section which tapers further than that of the first part of the nozzle element.

The third part of the nozzle element is preferably produced together with the first part of the nozzle element in a two-component method.

The third part of the nozzle element is advantageously made of a less resilient material than the first part of the nozzle element.

The object of the present invention is furthermore solved by means of an inhalation therapy device having a nebulising chamber and an aerosol generator which is arranged such that it releases an aerosol into the nebulising chamber, said aerosol generator comprising a nozzle element, with the nozzle element consisting of at least a first part, said first part of the nozzle element being made of a more resilient material than a member of the inhalation therapy device on which the nozzle element is moulded or to which the nozzle element is attached.

BRIEF DESCRIPTION OF THE DRAWINGS

The invention will be described in more detail below by means of embodiments and with reference to the drawings. In the drawings:

FIG. 2 shows a nozzle element according to the first embodiment of the present invention;

FIG. 3 shows a nozzle element according to a second embodiment of the present invention;

FIG. 4 shows a nozzle element according to a third embodiment of the present invention; and FIG. 5 shows a nozzle element according to a fourth embodiment of the present invention.

DETAILED DESCRIPTION OF THE PREFERRED EMBODIMENT(S)

Figure 1:
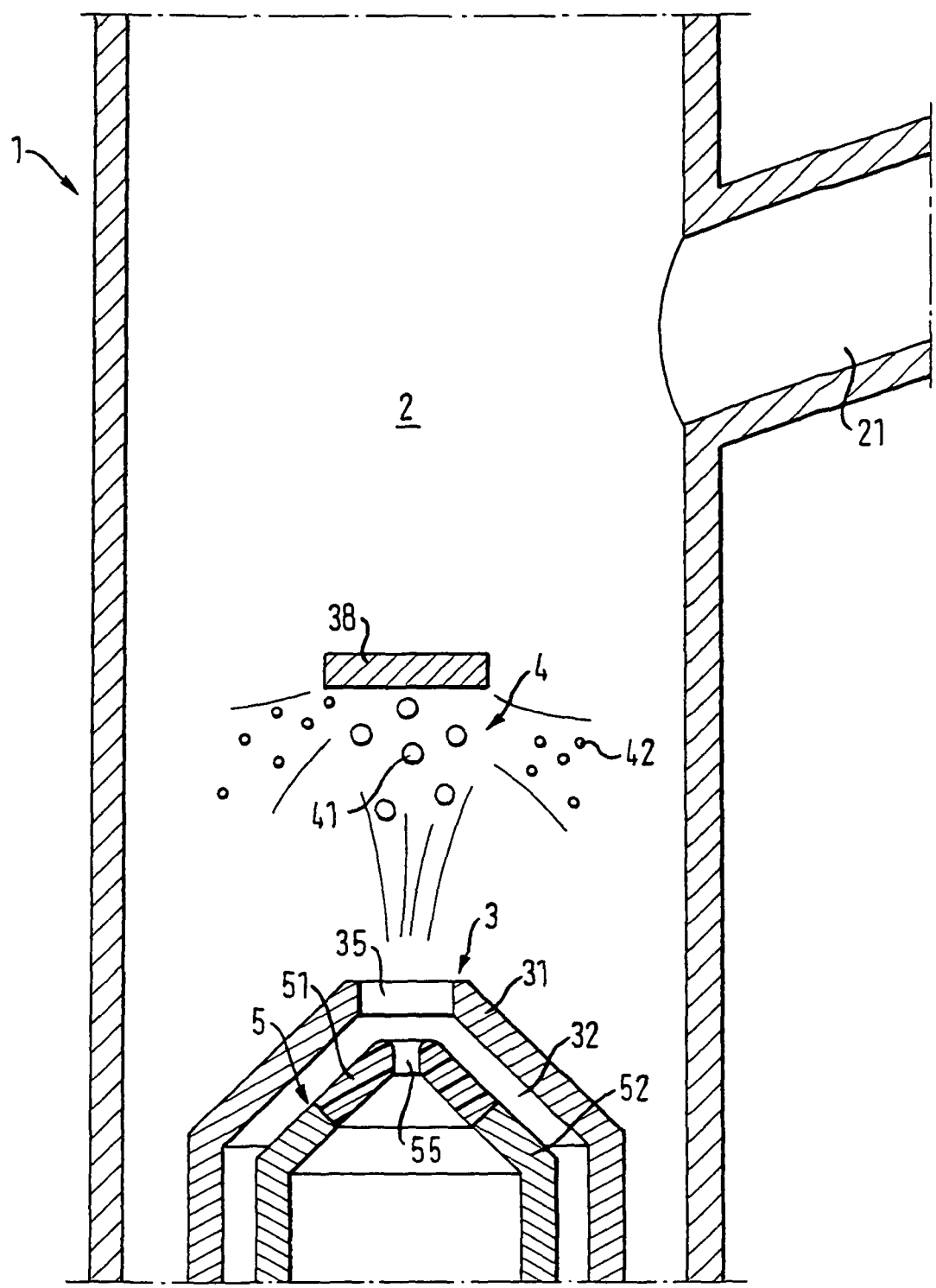
FIG. 1 shows an inhalation therapy device with an aerosol generator having a nozzle according to a first embodiment of the present invention.

FIG. 1 shows an inhalation therapy device 1 according to a first embodiment of the present invention. The inhalation therapy device comprises a nebulising chamber 2, attached to which is, for example, a mouthpiece 21 via which the patient can inhale the nebulised medicament in the form of an aerosol 4.

The inhalation therapy device can furthermore be provided with inhalation and exhalation valves (not shown here) such that a flow of respiratory air can be guided so as to achieve the optimum supply of an aerosol 4 to the patient. An aerosol generator 3 is provided in the nebulising chamber 2, which is able to generate an aerosol 4.

The aerosol generator 3 comprises a nozzle element 5, through which compressed air is guided in the present embodiment. The aerosol generator 3 furthermore comprises one or more channels 32, via which a medicament can be guided out of a storage container 6 and into the vicinity of the nozzle outlet 55 through which the compressed air guided by the nozzle element 5 escapes. The channels can, for example, be formed by means of a suitable member 31, which is designed such that one or more channels 32 are formed between the nozzle element 5 or the nozzle parts 51, 52 and the member 31. Owing to an injection or venturi effect, the medicament is sucked through the channels 32 and entrained by the compressed air which flows out of the nozzle outlet 55, such that a mixture of compressed air and medicament passes through the opening 35 of the member 31 and is released into the nebulising chamber 2.

In this embodiment, an impact baffle 38 is disposed in front of the opening 35 of the aerosol generator 3, said impact baffle having the object of controlling the air flow with the medicament such that when the medicament droplets collide with the impact baffle 38, an aerosol 4, 42 having a desired droplet spectrum is obtained. The droplets of the medicament 4, 41 exiting the aerosol generator 3 collide with the baffle 38, thereby resulting in a splitting of the aerosol droplets and making it possible to provide smaller aerosol droplets 4, 42. As a result of a corresponding air flow, which is generated by means of respiratory air supplied from the outside through a possibly present inhalation valve, the aerosol 4, 42 is entrained therewith and inhaled by the patient via the mouthpiece 21.

In the embodiment shown here, the nozzle body 5 of the aerosol generator 3 consists of a first part 51 and a second part 52, with the first part 51 of the nozzle element 5 having a cross-section which tapers further than that of the second part 52 of the nozzle element 5. The cross-section of the nozzle body is tapered further by the first part 51 of the nozzle element so that the cross-section decreases in the direction of the nozzle tip. In the embodiment shown here, the first part 51 of the nozzle element 5 comprises the nozzle rim or nozzle edge having the nozzle outlet 55. The first part 51 of the nozzle element 5 is made of a more resilient material than the second part 52 of the nozzle element 5 in this embodiment.

Within the meaning of the invention, resilience is to be understood as a material property which causes an element made from the material to resume its original shape of its own accord following deformation. This may, for example, be a silicone rubber or an elastomer that has this property, namely advantageously even in the case of a scratching stress, without incurring morphological damage, and resumes its original shape. A material is described as more resilient if, as compared to a less resilient material, it resumes its original form to a greater extent, virtually without any remaining deformation.

For cleaning of the aerosol generator 3, the member 31 can generally be removed so that the channels 32 for supplying the medicament are exposed, which improves the possibility for cleaning. Furthermore, the removal of the member 31 exposes the nozzle body such that it can be cleaned by a rinsing or cleaning liquid. Owing to the fact that the first part 51 of the nozzle element 5 is configured so as to be more resilient than the second-part 52 of the nozzle element 5, the upper, first part 51 of the nozzle element 5 can deform in a resilient manner during cleaning.

Since the resilient deformation of part 52 of the nozzle element 5 is a virtually completely reversible deformation, the first part 51 of the nozzle element 5 resumes the original shape following cleaning such that the original geometry of the nozzle is maintained, without damage occurring to the nozzle geometry. The first part 51 of the nozzle element 5 is attached to or moulded on the second part 52 of the nozzle element 5.

The at least two nozzle parts 51, 52 are fixedly connected to one another, as can be seen in the embodiment shown in FIG. 1, in order to prevent them from becoming detached from one another and to ensure a low friction or friction-free and low turbulence or turbulence-free transition.

In terms of production, the so-called two-component method (two-component injection moulding method), for example, is available for this purpose, with which it is possible for two or more suitable, albeit different materials, from which parts of an assembly are made, to be produced in injection moulding as a single part in an assembly. The parts of the assembly are then fixedly connected together and the transitions between one another can be connected almost without steps or indentations and essentially also without gaps. This ensures a low friction or friction-free and low turbulence or turbulence-free transition in the present case.

The second part 52 of the nozzle element 5 is made of a less resilient material than the first part 51 of the nozzle element 5, such that the deformability of the first part ensures a yielding during mechanical cleaning of the nozzle element 5, which essentially lowers the risk of damaging the nozzle element. The resilient material can thereby be a silicone rubber or a thermoplastic elastomer (TPE). The latter can be readily processed with less resilient materials, such as polyethylene (PE) or polypropylene (PP), in the two-component injection moulding method, such that the TPE parts and the PE or PP parts are fixedly connected together.

FIG. 2 shows an embodiment of the present invention in which the nozzle element 5 consists of a first part 51 and a second part 52. In this embodiment, the first part 51 contains the nozzle outlet 55. On account of the more resilient part 51 of the nozzle element 5 as compared to the less resilient part 52 of the nozzle element 5, the nozzle outlet 55 or the nozzle edge is reversibly deformable such that in the case of cleaning and a resulting deformation, part 51 of the nozzle element 5 can resume its original shape again as soon as the mechanical effect of cleaning no longer exists.

In a further advantageous embodiment, the part 51 of the nozzle element 5 can be designed such that by selecting a corresponding resilient material, the nozzle outlet 55 is widened in dependence on the flow of compressed air through said nozzle outlet 55, such that a stable state between the air flowing through and the medicament sucked through the channels 32 can be established in the aerosol generator 3. This embodiment is particularly advantageous if particles, which may possibly block the outlet 55, are already added to the compressed air during supply, so that the nozzle outlet is widened by the accumulated compressed air such that blocking of the nozzle outlet can be prevented. A further advantage of a part 51 designed in a resilient manner, which contains the nozzle outlet 55, is the simplified possibility of removing solid contaminating particles tightly adhering to or in the nozzle tip, which become detached when the resilient material is deformed. An improved cleaning is thus ensured. Owing to a resilient deformation of the nozzle outlet 55, solid particles blocking the nozzle outlet 55 can thus also be removed, without the geometry of the nozzle suffering lasting damage.

FIG. 3 shows an embodiment in which the nozzle body 5 comprises a third part 53. The third part 53 is again less resilient than the first part 51 of the nozzle element 5. In this embodiment, the third part 53 of the nozzle element 5 contains the nozzle outlet 55. The advantage of such an embodiment is that the nozzle outlet 55, or the rim surrounding the nozzle outlet, can be produced from a more dimensionally stable material, however owing to the more resilient part 51, can yield under pressure or as a result of other mechanical influences such that damage cannot occur to the upper part, in this case the third part 53, of the nozzle element 5. When cleaning the nozzle, the resilient part 51 of the nozzle element 5 deforms in the shown embodiment and, once the mechanical influence no longer exists, resumes the original shape again such that the dimensional stability of the nozzle is retained.

The demands on handlability, the mechanical effects to be endured and the stresses to be expected determine the selection of the material for the respective parts 51, 52 and 53, with it being assumed that the person skilled in the art will select suitable materials with suitable resiliences.

In the present invention, the boundary between the first part 51 of the nozzle element 5 and the second part of the nozzle element does not necessarily have to be in the top part of the nozzle element 5, as is shown in FIG. 4. The connecting region between the first part 51 of the nozzle element 5 and the second part 52 of the nozzle element 5 can rather also be in the bottom region of the nozzle element, which is attached, for example, to a housing part 11, without departing from the application area of the invention.

According to a further embodiment, the nozzle element can also be completely produced from a more resilient material than a component 11 of the inhalation therapy device on which the nozzle element 5 is formed or to which the nozzle element is attached. As shown in FIG. 5, the nozzle element can, for example, be configured as a plug-in type element which is inserted into a provided opening 15 during production. Production is thereby simplified and the nozzle element 5 can possibly be exchanged in the case of damage. Furthermore, the nozzle element 5 can take on sealing functions, for example in case of an attached tube supply 18.

The nozzle element 5 can thereby advantageously be made of a resilient material such as, for example, silicone rubber or a thermoplastic elastomer (TPE). The dimensional stability when in use is ensured by the member 31. When the member 31 is removed, the nozzle element 5 is exposed and, owing to its resilience, is not greatly exposed to a risk of damage during cleaning.

The invention claimed is:

1. An inhalation therapy device comprising:
   a nebulising chamber,
   an aerosol generator, which is arranged to release an aerosol into the nebulising chamber with a medicament, and which comprises a nozzle element and at least one medicament channel extending between the nozzle element and an outer member,
   said nozzle element comprising at least a first part and a second part, said first part of the nozzle element comprising a resilient deformable material, and including a deformable tip having a nozzle outlet comprising a nozzle edge configured to deliver a reproducible droplet spectrum of said aerosol through the nozzle outlet; the nozzle outlet being in fluid communication with the at least one medicament channel; said first part of the nozzle element being attached to said second part of the nozzle element and tapering from the second part with the cross-section of the first part converging to the deformable nozzle tip, and
   wherein said outer member is removable to expose portions of the at least one medicament channel; and
   wherein the nozzle outlet comprises a reversible deformable material configured to widen in dependence on flow through said nozzle outlet so that a stable state is established between the flow and medicament sucked into the flow.

2. An inhalation therapy device according to claim 1, wherein the first part of the nozzle element has a cross-section which tapers further than that of the second part of said nozzle element.

3. An inhalation therapy device according to one claim 1, wherein the first part of the nozzle element is made of silicone rubber or a thermoplastic elastomer (TPE).

4. An inhalation therapy device according to claim 1, wherein the first part of the nozzle element and the second part of said nozzle element comprises a two-component structure having said first part of the nozzle element molded on said second part of the nozzle element.

5. An inhalation therapy device according to claim 1, wherein the nozzle has a third part containing the nozzle outlet.

6. An inhalation therapy device according to claim 5, wherein the third part of the nozzle element and the first part of the nozzle element comprise a two-component molded structure.

7. An inhalation therapy device according to claim 1, wherein a third part of the nozzle element has a cross-section which tapers further than that of the first part of the nozzle element.

8. An inhalation therapy device according to claim 1, wherein the first part of the nozzle element consists of a material resuming original geometry following deformation.

9. An inhalation therapy device according to claim 1, wherein the outer member includes a portion converging to an opening aligned with the nozzle outlet and in fluid communication with the nozzle outlet.

10. An inhalation therapy device according to claim 1, the nozzle edge being reversibly deformable.

11. An inhalation therapy device comprising:
    a nebulising chamber;
    an aerosol generator, which is arranged to release an aerosol into the nebulising chamber with a medicament, and which comprises a nozzle element and at least one medicament channel extending between the nozzle element and an outer member;

said nozzle element comprising at least a first part and a second part, said first part of the nozzle element comprising a resilient deformable material, and including a deformable tip having a nozzle outlet comprising a nozzle edge configured to deliver a reproducible droplet spectrum of said aerosol through the nozzle outlet; the nozzle outlet being in fluid communication with the at least one medicament channel; said first part of the nozzle element being attached to said second part of the nozzle element and tapering from the second part with the cross-section of the first part converging to the deformable nozzle tip;

wherein said outer member is removable to expose portions of the at least one medicament channel, wherein the nozzle has a third part containing the nozzle outlet;

wherein the third part of the nozzle element is made of a less resilient material than the first part of said nozzle element.

12. An inhalation therapy device comprising:

a nebulising chamber, and an aerosol generator comprising a nozzle element mounted to a member, the aerosol generator being arranged such that the nozzle element releases an aerosol into the nebulising chamber, said nozzle element comprising at least a first part, said first part of the nozzle element comprising a reversibly deformable resilient nozzle tip, the nozzle tip forming a nozzle outlet comprising a nozzle edge around the nozzle outlet, the nozzle edge configured to deliver a reproducible droplet spectrum of said aerosol; the reversibly deformable resilient nozzle tip converging from the member to which the nozzle element is mounted to the nozzle edge;

wherein the nozzle outlet comprises a reversible deformable material configured to widen in dependence on flow through said nozzle outlet so that a stable state is established between the flow and medicament sucked into the flow.

13. An inhalation therapy device according to claim 12, wherein the first part of the nozzle element is made of silicone rubber or a thermoplastic elastomer (TPE).

14. An inhalation therapy device according to claim 12, wherein the first part of the nozzle element consists of a material resuming original geometry following deformation.

15. An inhalation therapy device according to claim 12, the nozzle edge being reversibly deformable.

16. An inhalation therapy device according to claim 12, wherein the nozzle element is molded to the member.

* * * * *